United States Patent
Miller et al.

(10) Patent No.: US 6,677,493 B1
(45) Date of Patent: Jan. 13, 2004

(54) PROCESSES FOR THE PURIFICATION AND USE OF 2-CHLORO-1,1,1,2,3,3,3-HEPTAFLUOROPROPANE AND ZEOTROPES THEREOF WITH HF

(75) Inventors: Ralph Newton Miller, Newark, DE (US); V. N. Mallikarjuna Rao, Wilmington, DE (US); Steven H. Swearingen, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 394 days.

(21) Appl. No.: 09/283,449

(22) Filed: Apr. 1, 1999

Related U.S. Application Data

(60) Provisional application No. 60/080,709, filed on Apr. 3, 1998.

(51) Int. Cl.[7] .................................................. C07C 19/08
(52) U.S. Cl. ............. 570/134; 252/182.11; 252/182.12; 252/182.32; 252/182.13
(58) Field of Search ...................... 570/134; 252/182.11, 252/182.12, 182.32, 182.13

(56) References Cited

U.S. PATENT DOCUMENTS

| | | | |
|---|---|---|---|
| 4,911,792 | A | 3/1990 | Manzer et al. |
| 5,057,634 | A | 10/1991 | Webster et al. |
| 5,068,472 | A | 11/1991 | Webster et al. |
| 5,276,225 | A | 1/1994 | Berthe |
| 5,364,992 | A | 11/1994 | Manogue et al. |

FOREIGN PATENT DOCUMENTS

| | | |
|---|---|---|
| EP | 0 434 408 A1 | 6/1991 |
| EP | 0 509 449 A2 | 10/1992 |
| EP | 0 509 885 A2 | 10/1992 |
| EP | 0 539 989 A1 | 5/1993 |
| EP | 0 542 290 A1 | 5/1993 |
| WO | WO 96/17813 | 6/1996 |

OTHER PUBLICATIONS

*The Condensed Dictionary*, 8th edition, Van Nostrand Reinhold Co., p. 8 (1971).*

* cited by examiner

Primary Examiner—Johann Richter
Assistant Examiner—Elvis O. Price

(57) ABSTRACT

A process is disclosed for the separation of a mixture of HF and $CF_3CClFCF_3$. The process involves placing the mixture in a separation zone at a temperature of from about –30° C. to about 100° C. and at a pressure sufficient to maintain the mixture in the liquid phase, whereby an organic-enriched phase comprising less than 50 mole percent HF is formed as the bottom layer and an HF-enriched phase comprising more than 90 mole percent HF is formed as the top layer. The organic-enriched phase can be withdrawn from the bottom of the separation zone and subjected to distillation in a distillation column to recover essentially pure $CF_3CClFCF_3$. The distillate comprising HF and $CF_3CClFCF_3$ can be removed from the top of the distillation column while essentially pure $CF_3CClFCF_3$ can be recovered from the bottom of the distillation column. The HF-enriched phase can be withdrawn from the top of the separation zone and subjected to distillation in a distillation column. The distillate comprising HF and $CF_3CClFCF_3$ can be removed from the top of the distillation column while essentially pure HF can be recovered from the bottom of the distillation column. If desired, the two distillates can be recycled to the separation zone.

Also disclosed are compositions of hydrogen fluoride in combination with an effective amount of $CF_3CClFCF_3$ to form an azeotrope or azeotrope-like composition with hydrogen fluoride. Included are compositions containing from about 38.4 to 47.9 mole percent $CF_3CClFCF_3$.

Also disclosed are processes for producing 1,1,1,2,3,3,3-heptafluoro-propane. One process uses a mixture comprising HF and $CF_3CClFCF_3$ and is characterized by preparing essentially pure $CF_3CClFCF_3$ as indicated above, and reacting the $CF_3CClFCF_3$ with hydrogen. Another process uses an azeotropic composition as described above, and reacts the $CF_3CClFCF_3$ with hydrogen in the presence of HF.

Also disclosed is a process for producing hexafluoropropene. This process is characterized by preparing essentially pure $CF_3CClFCF_3$ as indicated above, and dehalogenating the $CF_3CClFCF_3$.

19 Claims, 1 Drawing Sheet

PROCESSES FOR THE PURIFICATION AND USE OF 2-CHLORO-1,1,1,2,3,3,3-HEPTAFLUOROPROPANE AND ZEOTROPES THEREOF WITH HF

This application claims the priority benefit of U.S. Provisional application 60/080,709, filed Apr. 3, 1998.

FIELD OF THE INVENTION

This invention relates to the purification of 2-chloro-1,1,1,2,3,3,3-heptafluoropropane (i.e., $CF_3CClFCF_3$ or CFC-217ba), its azeotropic compositions with hydrogen fluoride and their use in separation processes.

BACKGROUND

Hexafluoropropylene (i.e., $CF_3CF=CF_2$ or HFP), a valuable fluoromonomer can be prepared by the hydrodehalogenation of $CF_3CClFCF_3$ which itself can be prepared by the reaction of $CF_3CCl_2CF_3$ (CFC-216aa) with HF (see e.g., U.S. Pat. Nos. 5,057,634 and 5,068,472). Typically excess HF is used to obtain favorable reaction rates for the conversion of CFC-216aa to CFC-217ba. HF may be removed from the halogenated hydrocarbon components of the product mixture using conventional aqueous solution scrubbing techniques. However, the production of substantial amounts of scrubbing discharge can create aqueous waste disposal concerns.

There remains a need for processes that utilize HF in such product mixtures in an environmentally benign manner.

SUMMARY OF THE INVENTION

This invention provides a process for the separation of a mixture comprising HF and $CF_3CClFCF_3$. The process comprises placing the mixture in a separation zone at a temperature of from about $-30°$ C. to about $100°$ C. and at a pressure sufficient to maintain the mixture in the liquid phase, whereby an organic-enriched phase comprising less than 50 mole percent HF is formed as the bottom layer and an HF-enriched phase comprising more than 90 mole percent HF is formed as the top layer.

The organic-enriched phase can be withdrawn from the bottom of the separation zone and subjected to distillation in a distillation column to recover essentially pure $CF_3CClFCF_3$. The distillate comprising HF and $CF_3CClFCF_3$ can be removed from the top of the distillation column, while $CF_3CClFCF_3$ which is essentially free of HF can be recovered from the bottom of the distillation column. If desired, the distillate can be recycled to the separation zone.

The HF-enriched phase can be withdrawn from the top of the separation zone and subjected to distillation in a distillation column. The distillate comprising HF and $CF_3CClFCF_3$ can be removed from the top of the distillation column while essentially pure HF can be recovered from the bottom of the distillation column. If desired, the distillate can be recycled to the separation zone.

Also provided are compositions which comprise hydrogen fluoride in combination with an effective amount of $CF_3CClFCF_3$ to form an azeotrope or azeotrope-like composition with hydrogen fluoride, said composition containing from about 38.4 to 47.9 mole percent $CF_3CClFCF_3$.

Also provided is a process for producing 1,1,1,2,3,3,3-heptafluoropropane from a mixture comprising HF and $CF_3CClFCF_3$. The process is characterized by preparing $CF_3CClFCF_3$ which is essentially free of HF as indicated above, and reacting said $CF_3CClFCF_3$ with hydrogen.

Also provided is another process for producing 1,1,1,2,3,3,3-heptafluoropropane. This process is characterized by contacting an azeotrope of $CF_3CClFCF_3$ and HF as described above with hydrogen, and reacting the $CF_3CClFCF_3$ with hydrogen in the presence of HF.

Also provided is a process for producing hexafluoropropene from a mixture of comprising HF and $CF_3CClFCF_3$. The process is characterized by preparing $CF_3CClFCF_3$ which is essentially free of HF as indicated above, and dehalogenating the $CF_3CClFCF_3$.

DETAILED DESCRIPTION

Figure 1:
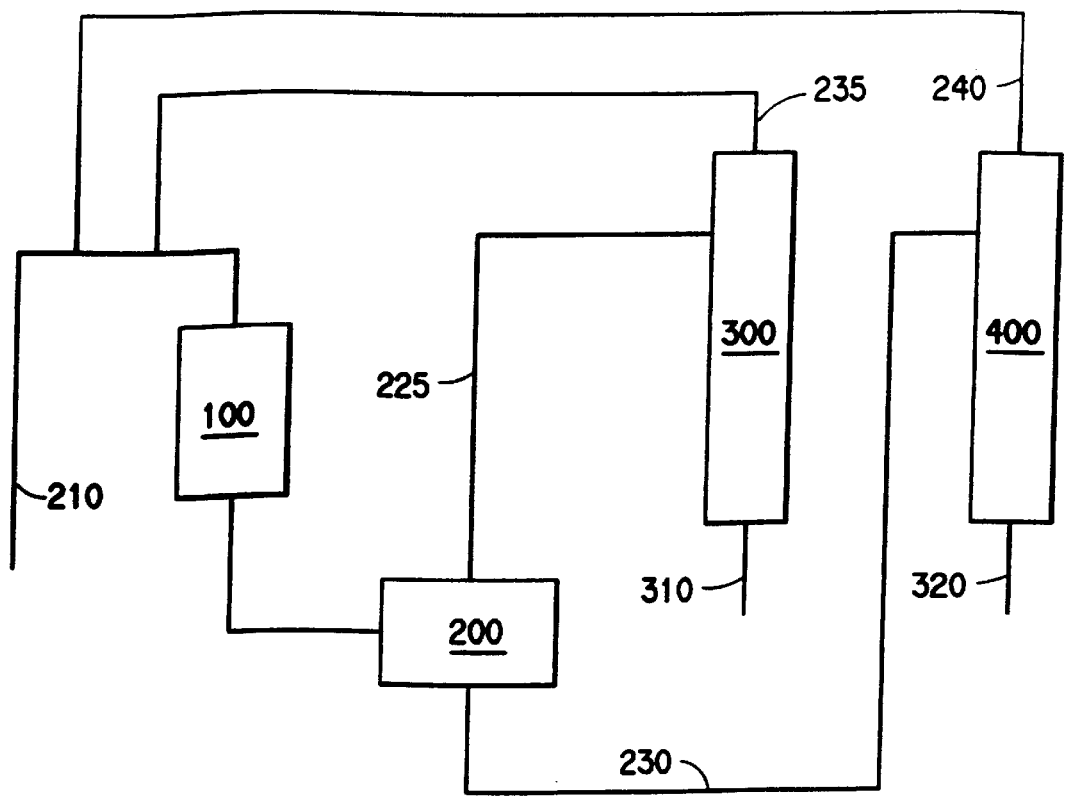
FIG. 1 is a schematic flow diagram of an embodiment of the purification process of this invention, namely an azeotrope separation process.

FIG. 1 is illustrative of one method of practicing a separation process in accordance with this invention. Referring to FIG. 1, a feed mixture comprising HF and CFC-217ba with a HF:CFC-217ba molar ratio of greater than about 1:1, is passed through line (210) though cooler (100) to a separation zone (200). The feed mixture might, for example, be derived from a reactor for synthesizing CFC-217ba by the hydrofluorination of CFC-216aa, and feed line (210) might follow an HCl removal column (not shown). The separation zone (200) is held at a temperature of from between about $-30°$ C. and about $100°$ C, preferably from between about $-25°$ C. to about $0°$ C., and at a pressure sufficient to keep the mixture as a liquid. For example, at about $50°$ C. the separator is maintained at a pressure greater than about 117 psia (806 kPa), and at about $-20°$ C. the separator is maintained at a pressure greater than about 10 psia (69 kPa). At these temperatures, the liquefied stream forms two phases, one phase organic-enriched compared to the feed mixture, the other phase HF-enriched compared to the feed mixture. The organic-rich phase typically contains more than 50 mole % organic; the HF-rich phase typically contains more than 90 mole % HF. Within the preferred temperature range of $-25°$ C. to $0°$ C., the organic-rich phase typically contains 10 mole percent HF, or less, and the HF-rich phase typically contains 95 mole percent HF, or more.

The HF-rich phase is removed through line (225) from the top of the separation zone (200) and fed to a multiple stage distillation column (300) operated under conditions such that a lower boiling azeotropic or azeotrope-like mixture is formed comprising HF and CFC-217ba. The column (300) operating pressure is typically between from about 10 psia (69 kPa) to about 250 psia (1723 kPa) and the temperature at the column top is typically between from about $0°$ C. to about $100°$ C., but with the exact temperature being dependent on the operating pressure. The HF/CFC-217ba azeotrope is distilled overhead and removed from the top of the column (300) through line (235) and recycled back to the cooler (100). Essentially pure HF can be removed from the bottom the distillation column though line (310).

The organic-rich phase is removed from the bottom of the separation zone (200) through line (230) and fed to another multistage distillation column (400) operated under conditions such that a low boiling azeotropic or azeotrope-like composition comprising HF and CFC-217ba is formed. The column (400) operating pressure is typically between from about 10 psia (69 kPa) to about 250 psia (1723 kPa) and the temperature at the column top is typically between from about $0°$ C. to about $100°$ C., but with the exact temperature being dependent on the operating pressure. The HF/CFC-217ba azeotrope is distilled overhead and removed from the top of the column (400) through line (240) and recycled to the cooler (100). Essentially pure CFC-217ba is removed from the bottom of the column through line (320).

As noted above, CFC-217ba may be reacted with hydrogen to form $CF_3CHFCF_3$. Examples of this process include processes where CFC-217ba is reacted with hydrogen at an elevated temperature of about 300° C. or less in the presence of a hydrogenation catalyst. Also included are processes where CFC-217ba is reacted with hydrogen without a catalyst at a temperature within the range of about 350° C. to 700° C.

Those skilled in the art will recognize that since the drawings are representational, it will be necessary to include further items of equipment in an actual commercial plant, such as pressure and temperature sensors, pressure relief and control valves, compressors, pumps, storage tanks and the like. The provision of such ancillary items of equipment would be in accordance with conventional chemical engineering practice.

The above embodiment of this invention involves azeotropic distillation of mixtures of HF and $CF_3CClFCF_3$ (CFC-217ba). The product mixtures distilled in accordance with this invention can be obtained from a variety of sources. These sources include product mixtures obtained by hydrofluorination of $CF_3CCl_2CF_3$ to $CF_3CClFCF_3$.

Of note is a process wherein $CF_3CClFCF_3$ is purified from a mixture which consists essentially of hydrogen fluoride in combination with an effective amount of $CF_3CClFCF_3$ to form an azeotrope or azeotrope-like composition with hydrogen fluoride, said azeotropic composition containing from about 38.4 to 47.9 mole percent $CF_3CClFCF_3$.

The present invention also provides compositions which consist essentially of hydrogen fluoride and an effective amount of $CF_3CClFCF_3$ to form an azeotropic combination with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature may be higher or lower than the boiling temperatures of the individual components, and which will provide a vapor composition essentially identical to the liquid composition undergoing boiling.

An azeotrope is a liquid mixture that exhibits a maximum or minimum boiling point relative to the boiling points of surrounding mixture compositions. An azeotrope is homogeneous if only one liquid phase is present. An azeotrope is heterogeneous if more than one liquid phase is present. Regardless, a characteristic of minimum boiling azeotropes is that the bulk liquid composition is then identical to the vapor composition in equilibrium therewith, and distillation of the azeotropic mixture is ineffective as a separation technique. For the purpose of this discussion, azeotrope-like composition means a composition which behaves like an azeotrope (i.e., has constant-boiling characteristics or a tendency not to fractionate upon boiling or evaporation). Thus, the composition of the vapor formed during boiling or evaporation of such compositions is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte, Ind. Eng. Chem. Process Des. Dev. 1980, 19, pp 432–439). Experimental identification of azeotropic compositions involving the same components may be used to confirm the accuracy of such calculations and/or to modify the calculations for azeotropic compositions at the same or other temperatures and pressures.

Compositions may be formed which consist essentially of azeotropic combinations of hydrogen fluoride with $CF_3CClFCF_3$. These include a composition consisting essentially of from about 61.6 to about 52.1 mole percent HF and from about 38.4 to 47.9 mole percent $CF_3CClFCF_3$ (which forms an azeotrope boiling at a temperature from between about −50° C. and about 50° C. and a pressure between about 13.1 kPa and about 807 kPa).

At atmospheric pressure, the boiling points of hydrofluoric acid and CFC-217ba are about 19.5° C. and −2.2° C., respectively. The relative volatility at 9.7 psia (67 kPa) and −20° C. of HF and CFC-217ba was found to be nearly 1.0 as 60.4 mole percent HF and 39.6 mole percent CFC-217ba was approached. The relative volatility at 56.0 psia (386 kPa) and 25° C. of HF and CFC-217ba was found to be nearly 1.0 as 55.7 mole percent HF and 44.3 mole percent CFC-217ba was approached. These data indicate that the use of conventional distillation procedures will not result in the separation of a substantially pure compound because of the low value of relative volatility of the compounds.

To determine the relative volatility of HF with each of CFC-217ba, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", 4th Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and CFC-217ba behave in an ideal manner, and can sufficiently predict the relative volatilities of the components in such mixtures. Thus, while HF has a good relative volatility compared to CFC-217ba at low CFC-217ba concentrations, the relative volatility becomes nearly 1.0 as 39.6 mole percent CFC-217ba was approached at −20° C. This would make it impossible to separate CFC-217ba from HF by conventional distillation from such a mixture. Where the relative volatility approaches 1.0 defines the system as forming a near-azeotrope. Where the relative volatility is 1.0 defines the system as forming an azeotrope.

It has been found that azeotropes of HF and CFC-217ba are formed at a variety of temperatures and pressures. At a pressure of 9.7 psia (67.0 kPa) and −20° C., the azeotrope vapor composition was found to be about 60.4 mole percent HF and about 39.6 mole percent CFC-217ba. At a pressure of 56.0 psia (386 kPa) and 25° C., the azeotrope vapor composition was found to be about 55.7 mole percent HF and about 44.3 mole percent CFC-217ba. Based upon the above findings, it has been calculated that an azeotropic composition of about 61.6 mole percent HF and about 38.4 mole percent CFC-217ba can be formed at −50° C. and 1.91 psia (13.1 kPa) and an azeotropic composition of about 52.1 mole percent HF and about 47.9 mole percent CFC-217ba can be formed at 50° C. and 117 psia (807 kpa). Accordingly, the present invention provides an azeotrope or azeotrope-like composition consisting essentially of from about 61.6 to 52.1 mole percent HF and from about 38.4 to 47.9 mole percent CFC-217ba, said composition having a boiling point from about −50° C. at 13.1 kPa to about 50° C. at 807 kPa.

The CFC-217ba/HF azeotrope is useful as recycle to the fluorination reactor, where the recycled HF can function as a reactant and the recycled CFC-217ba can function to moderate the temperature effect of the heat of reaction. CFC-217ba can be reacted with HF to produce perfluoropropane (i.e., $CF_3CF_2CF_3$ or FC-218). It will also be apparent to one of ordinary skill in the art that distillation including azeotropes with HF can typically be run under more convenient conditions than distillation without HF, e.g., where HF is removed prior to distillation. HF may be removed from the halogenated hydrocarbon components of the product mixture using conventional aqueous solution scrubbing techniques. However, the production of substantial amounts of scrubbing discharge can create aqueous waste disposal concerns. Thus, there remains a need for processes utilizing HF in such product mixtures.

CFC-217ba (essentially free of HF or as an azeotrope with HF) can be hydrogenolyzed to HFC-227ea (i.e., $CF_3CHFCF_3$) either in the presence or the absence of a catalyst. CFC-217ba can be hydrodechlorinated to HFC-227ea by a process comprising contacting CFC-217ba and hydrogen in the presence of a catalyst selected from the group consisting of rhenium, ruthenium, rhodium and palladium, and mixtures thereof at a temperature of at least 100° C. and a pressure within the range of from about 101 kPa to about 5000 kPa. U.S. Pat. No. 5,364,992 discloses a process for the hydrogenolysis of CFC-217ba to HFC-227ea by contacting CFC-217ba with at least 0.1 mole of hydrogen per mole of CFC-217ba in an empty reaction vessel of nickel, iron or their alloys at a pressure within the range of from 0 psig (101 kPa) to 1000 psig (6994 kPa), at a temperature within the range of from 350° C. to 700° C. and for a time sufficient to produce HFC-227ea.

CFC-217ba can be dehalogenated to $CF_2=CFCF_3$. Dehalogenation is conducted using hydrogen and suitable catalyst (see e.g., U.S. Pat. Nos. 5,057,634 and 5,068,472).

While the initial mixture treated in accordance with the present invention can be obtained from a variety of sources, including by adding CFC-217ba to HF-containing compositions, an advantageous use of the instant invention resides in treating the effluent mixtures from the preparation of CFC-217ba as described above. Generally, the reaction effluents have a molar ratio of HF:CFC-217ba from about 0.1:1 to about 100:1. The preferred HF:CFC-217ba molar ratio is from about 1:1 to 10:1 for vapor phase fluorination reactions and about 1:1 to about 50:1 for liquid phase reactions. The most preferred HF:CFC-217ba molar ratio is from about 2:1 to 5:1 to achieve maximum benefit from the instant process. When the initial mixture treated in accordance with the invention also contains HCl and other low-boilers (e.g., $C_3F_8$), the HAL and other low-boilers can be removed in another distillation column before feeding the mixture to the azeotrope separation columns.

High-boilers, if present, can be removed in an independent distillation column after separation of HF from CFC-217ba.

The distillation equipment and its associated feed lines, effluent lines and associated units should be constructed of materials resistant to hydrogen fluoride, hydrogen chloride and chlorine. Typical materials of construction, well-known to the fluorination art, include stainless steels, in particular of the austenitic type, and the well-known high nickel alloys, such as Monel® nickel-copper alloys, Hastelloy® nickel-based alloys and, Inconel® nickel-chromium alloys. Also suitable for reactor fabrication are such polymeric plastics as polytrifluoro chloroethylene and polytetrafluoroethylene, generally used as linings.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

EXAMPLES

| Legend | |
|---|---|
| 23 is $CHF_3$ | 115 is $CClF_2CF_3$ |
| 125 is $CHF_2CF_3$ | 216aa is $CF_3CCl_2CF_3$ |
| 216ba is $CClF_2CClFCF_3$ | 217ba is $CF_3CClFCF_3$ |
| 217ca is $CClF_2CFCF_3$ | 218 is $CF_3CF_2CF_3$ |
| 226da is $CF_3CHClCF_3$ | 227ea is $CF_3CHFCF_3$ |
| 1214 is $C_3Cl_2F_4$ | 1215 is $C_3ClF_5$ |
| T is temperature | |

Example 1

In the following example, all values for the compounds are in moles per unit time and temperatures are in degrees Celsius. The data were obtained by calculation using measured and calculated thermodynamic properties. The numbers at the top of the columns refer to FIG. 1.

| Compound | 210 Feed Mixture | 100 Cooler Feed | 200 Decanter Feed | 225 HF-Rich Phase | 230 Organic-Rich Phase |
|---|---|---|---|---|---|
| HF | 60 | 63.2 | 63.2 | 62.5 | 0.67 |
| 217ba | 10 | 12.6 | 12.6 | 1.26 | 11.3 |
| Temp. ° C. | 50 | 47.9 | 0 | 0.0 | 0.0 |
| Press. KPa (psia) | 791 (114.7) | 791 (114.7) | 722 (104.7) | 860 (124.7) | 860 (124.7) |

| Compound | 235 HF Col. Dist. | 310 HF Col. Tails | 240 Org. Col. Dist. | 320 Org. Col. Tails |
|---|---|---|---|---|
| HF | 2.52 | 60 | 0.67 | <0.01 |
| 217ba | 1.26 | <0.01 | 1.34 | 10.0 |
| Temp. ° C. | 53.9 | 92.6 | 54.2 | 68.6 |
| Press. KPa (psia) | 860 (124.7) | 873 (126.7) | 860 (124.7) | 873 (126.7) |

Example 2

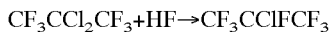

Chromium oxide (47.25 g, 35 mL, 10–20 mesh, (2.0–0.84 mm)), obtained from the pyrolysis of ammonium dichromate prepared according to the procedure described in U.S. Pat. No. 5,036,036, was placed in a ⅝" (1.58 cm) diameter Inconel® nickel alloy reactor heated in a fluidized sand bath. It was heated to 175° C. in a flow of nitrogen (50 cc/min) at which time HF flow (50 cc/min) was also started through the reactor. After 15 minutes, the nitrogen flow was decreased to 20 cc/min and the HF flow increased to 80 cc/min. The reactor temperature was gradually increased to 400° C. during a 2 hour period and maintained at 400° C. for an additional 30 minutes. At the end of this period the reactor was brought to the desired operating temperature for catalyst evaluation under a nitrogen flow.

The contact time for each run was 30 seconds. The results of the fluorination reaction are shown in Table 2 in mol %.

TABLE 2

| T ° C. | Molar Ratio HF:216aa | % 218 | % 217ba | % 1215 | % 226da | % 216aa | % Others |
|---|---|---|---|---|---|---|---|
| 375 | 4:1 | 0.2 | 7.4 | 0.6 | 0.7 | 90.2 | 0.8 |
| 400 | 4:1 | 0.6 | 18.2 | 0.7 | 0.9 | 78.7 | 0.9 |
| 400 | 8:1 | 0.6 | 22.2 | 1.0 | 0.9 | 74.5 | 0.8 |
| 400 | 12:1 | 0.6 | 23.8 | 1.3 | 0.9 | 72.4 | 0.9 |
| 400 | 20:1 | 0.6 | 28.2 | 1.8 | 1.7 | 66.5 | 1.2 |
| 425 | 20:1 | 1.3 | 53.7 | 1.6 | 1.7 | 39.7 | 1.9 |

Others include mostly 23, 115, 125, 1214, 227ea, 216ba and 217ca.

Example 3

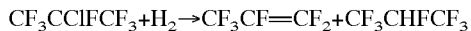

A 15"(38.1 cm)×⅜" (0.95 cm) O.D. Inconel™ 600 nickel alloy U-tube reactor was charged with 1% Ru/Acid-Washed Carbon (1.9 g, 6.25 Ml. The reaction pressure was 0 psig (101.3 kPa). Results (in mol %) at various conditions are shown in Table 3.

TABLE 3

| T ° C. | Mol $H_2$:217ba | CT min. | % Conv 217ba | % Sel. HFP | % Sel. 227ea | % Sel. 226ea | % Sel. Other |
|---|---|---|---|---|---|---|---|
| 200 | 4 | 0.30 | 84 | 7 | 74 | 5 | 13 |
| 175 | 4 | 0.32 | 46 | 10 | 72 | 4 | 15 |
| 213 | 2 | 0.30 | 81 | 9 | 75 | 6 | 9 |
| 200 | 1 | 0.31 | 50 | 15 | 74 | 5 | 6 |

What is claimed is:

1. A composition comprising hydrogen fluoride in combination with an effective amount of $CF_3CClFCF_3$ to form an azeotrope or azeotrope-like composition said composition containing from about 38.4 to 47.9 mole percent $CF_3CClFCF_3$.

2. A process for the separation of a composition of claim 1 comprising HF and $CF_3CClFCF_3$, comprising:
(a) placing said composition in a separation zone at a temperature of from about −30° C. to about 100° C. and at a pressure sufficient to maintain the composition in the liquid phase, whereby an organic-enriched phase comprising less than 50 mole percent HF is formed as the bottom layer and an HF-enriched phase comprising more than 90 mole percent HF is formed as the top layer;
(b1) withdrawing the organic-enriched phase from the bottom of the separation zone and distilling it in a distillation column;
(c1) removing the distillate comprising HF and $CF_3CClFCF_3$ from the top of the distillation column of (b1); and
(d1) recovering $CF_3CClFCF_3$ which is essentially free of HF from the bottom of the distillation column.

3. The process of claim 2 wherein the separation zone is operated at a temperature of from −25° C. to 0° C., to form an organic-enriched phase containing 10 mole percent HF, or less and an HF-enriched phase containing 95 mole percent HF, or more.

4. The process of claim 2 wherein the distillate removed in (c1) is recycled to the separation zone.

5. A process for the separation of a composition of claim 1 comprising HF and $CF_3CClFCF_3$, comprising:
(a) placing said composition in a separation zone at a temperature of from about −30° C. to about 100° C. and at a pressure sufficient to maintain the composition in the liquid phase, whereby an organic-enriched phase comprising less than 50 mole percent HF is formed as the bottom layer and an HF-enriched phase comprising more than 90 mole percent HF is formed as the top layer;
(b2) withdrawing the HF-enriched phase from the top of the separation zone and distilling it in a distillation column;
(c2) removing the distillate comprising HF and $CF_3CClFCF_3$ from the top of the distillation column of (b2); and
(d2) recovering essentially pure HF from the bottom of the distillation column of (b2).

6. The process of claim 5 wherein the distillate removed in (c2) is recycled to the separation zone.

7. The process of claim 6 further comprising (b1) withdrawing the organic-enriched phase from the bottom of the separation zone and distilling it in a distillation column; (c1) removing the distillate comprising HF and $CF_3CClFCF_3$ from the top of the distillation column of (b1); and (d1) recovering $CF_3CClFCF_3$ which is essentially free of HF from the bottom of the distillation column.

8. A process for producing 1,1,1,2,3,3,3-heptafluoropropane from a composition of claim 1 comprising HF and $CF_3CClFCF_3$, characterized by:

(a) placing said composition in a separation zone at a temperature of from about −30° C. to about 100° C. and at a pressure sufficient to maintain the composition in the liquid phase, whereby an organic-enriched phase comprising less than 50 mole percent HF is formed as the bottom layer and an HF-enriched phase comprising more than 90 mole percent HF is formed as the top layer;

(b1) withdrawing the organic-enriched phase from the bottom of the separation zone and distilling it in a distillation column;

(c1) removing the distillate comprising HF and $CF_3CClFCF_3$ from the top of the distillation column of (b1);

(d1) recovering $CF_3CClFCF_3$ which is essentially free of HF from the bottom of the distillation column; and (e) reacting said $CF_3CClFCF_3$ from (d1) with hydrogen.

9. A process for producing 1,1,1,2,3,3,3-heptafluoropropane from a composition of claim 1 comprising HF and $CF_3CClFCF_3$, characterized by:

contacting said composition with hydrogen; and reacting the $CF_3CClFCF_3$ with hydrogen in the presence of HF.

10. A process for producing hexafluoropropene from a composition of claim 1 comprising HF and $CF_3CClFCF_3$, characterized by:

(a) placing said composition in a separation zone at a temperature of from about −30° C. to about 100° C. and at a pressure sufficient to maintain the composition in the liquid phase, whereby an organic-enriched phase comprising less than 50 mole percent HF is formed as the bottom layer and an HF-enriched phase comprising more than 90 mole percent HF is formed as the top layer;

(b1) withdrawing the organic-enriched phase from the bottom of the separation zone and distilling it in a distillation column;

(c1) removing the distillate comprising HF and $CF_3CClFCF_3$ from the top of the distillation column of (b1);

(d1) recovering $CF_3CClFCF_3$ which is essentially free of HF from the bottom of the distillation column; and (e) dehydrohalogenating the $CF_3CClFCF_3$ from (d1).

11. A process for the separation of a mixture comprising HF and $CF_3CClFCF_3$, comprising:

(a) placing the mixture in a separation zone at a temperature of from about −30° C. to about 100° C. and at a pressure sufficient to maintain the mixture in the liquid phase, whereby an organic-enriched phase comprising less than 50 mole percent HF is formed as the bottom layer and an HF-enriched phase comprising more than 90 mole percent HF is formed as the top layer;

(b1) withdrawing the organic-enriched phase from the bottom of the separation zone and distilling it in a distillation column;

(c1) removing the distillate as a composition of claim comprising HF and $CF_3CClFCF_3$ from the top of the distillation column of (b1) and recycling said composition to the separation zone; and (d1) recovering $CF_3CClFCF_3$ which is essentially free of HF from the bottom of the distillation column.

12. The process of claim 11 wherein the separation zone is operated at a temperature of from −25° C. to 0° C., to form an organic-enriched phase containing 10 mole percent HF, or less and an HF-enriched phase containing 95 mole percent HF, or more.

13. A process or the separation of a mixture comprising HF and $CF_3CClFCF_3$, comprising:

(a) placing the mixture in a separation zone at a temperature of from about −30° C. to about 100° C. and at a pressure sufficient to maintain the mixture in the liquid phase, whereby an organic-enriched phase comprising less than 50 mole percent HF is formed as the bottom layer and an HF-enriched phase comprising more than 90 mole percent HF is formed as the top layer;

(b2) withdrawing the HF-enriched phase from the top of the separation zone and distilling it in a distillation column;

(c2) removing the distillate as a composition of claim 1 comprising HF and $CF_3CClFCF_3$ from the top of the distillation column of (b2) and recycling said composition to the separation zone; and (d2) recovering essentially pure HF from the bottom of the distillation column of (b2).

14. The process of claim 13 further comprising (b1) withdrawing the organic-enriched phase from the bottom of the separation zone and distilling it in a distillation column;

(c1) removing the distillate comprising HF and $CF_3CClFCF_3$ from the top of the distillation column of (b1); and (d1), recovering $CF_3CClFCF_3$ which is essentially free of HF from the bottom of the distillation column.

15. A process for producing 1,1,1,2,3,3,3-heptafluoropropane from a mixture comprising HF and $CF_3CClFCF_3$, characterized by:

(a) placing the mixture in a separation zone at a temperature of from about −30° C. to about 100° C. and at a pressure sufficient to maintain the mixture in the liquid phase, whereby an organic-enriched phase comprising less than 50 mole percent HF is formed as the bottom layer and an HF-enriched phase comprising more than 90 mole percent HF is formed as the top layer;

(b1) withdrawing the organic-enriched phase from the bottom of the separation zone and distilling it in a distillation column;

(c1) removing the distillate as a composition of claim 1 comprising HF and $CF_3CClFCF_3$ from the top of the distillation column of (b1) and recycling said composition to the separation zone;

(d1) recovering $CF_3CClFCF_3$ which is essentially free of HF from the bottom of the distillation column; and (e) reacting said $CF_3CClFCF_3$ from (d1) with hydrogen.

16. A process for producing hexafluoropropene from a mixture comprising HF and $CF_3CClFCF_3$, characterized by:

(a) placing the mixture in a separation zone at a temperature of from about −30° C. to about 100° C. and at a pressure sufficient to maintain the mixture in the liquid phase, whereby an organic-enriched phase comprising less than 50 mole percent HF is formed as the bottom layer and an HF-enriched phase comprising more than 90 mole percent HF is formed as the top layer;

(b1) withdrawing the organic-enriched phase from the bottom of the separation zone and distilling it in a distillation column;

(c1) removing the distillate as a composition of claim 1 comprising HF and $CF_3CClFCF_3$ from the top of the distillation column of (b1) and recycling said composition to the separation zone;

(d1) recovering $CF_3CClFCF_3$ which is essentially free of HF from the bottom of the distillation column; and (e) dehydrohalogenating the $CF_3CClFCF_3$ from (d1).

17. A composition of claim 1 which contains from about 61.6 to 52.1 mole percent HF.

18. A composition which consists essentially of an azeotropic combination of hydrogen fluoride with $CF_3CClFCF_3$.

19. An azeotrope or azeotrope-like composition which consists essentially of from about 61.6 to 52.1 mole percent HF and from about 38.4 to 47.9 mole percent $CF_3CClFCF_3$, said composition having a boiling point from about about −50° C. at 1.91 psia to about 50° C. at 117 psia.

* * * * *